United States Patent
Ang et al.

(10) Patent No.: US 9,357,938 B2
(45) Date of Patent: Jun. 7, 2016

(54) METHOD AND SYSTEM FOR MOTOR REHABILITATION

(75) Inventors: Kai Keng Ang, Singapore (SG); Cuntai Guan, Singapore (SG); Sui Geok Karen Chua, Singapore (SG); Chuanchu Wang, Singapore (SG); Hock Guan Adrian Tan, Singapore (SG); Kok Soon Phua, Singapore (SG); Haihong Zhang, Singapore (SG); Zheng Yang Chin, Singapore (SG)

(73) Assignees: Agency for Science, Technology and Research, Singapore (SG); Tan Tock Seng Hospital Pte Ltd, Singapore (SG)

( * ) Notice: Subject to any disclaimer, the term of this patent is extended or adjusted under 35 U.S.C. 154(b) by 839 days.

(21) Appl. No.: 13/638,352

(22) PCT Filed: Mar. 31, 2011

(86) PCT No.: PCT/SG2011/000137
§ 371 (c)(1),
(2), (4) Date: Feb. 8, 2013

(87) PCT Pub. No.: WO2011/123072
PCT Pub. Date: Oct. 6, 2011

(65) Prior Publication Data
US 2014/0018694 A1  Jan. 16, 2014

Related U.S. Application Data

(63) Continuation-in-part of application No. PCT/SG2010/000127, filed on Mar. 31, 2010.

(60) Provisional application No. 61/319,452, filed on Mar. 31, 2010.

(51) Int. Cl.
*A61B 5/04*  (2006.01)
*A61B 5/048*  (2006.01)
(Continued)

(52) U.S. Cl.
CPC ............ *A61B 5/04014* (2013.01); *A61B 5/048* (2013.01); *A61B 5/04017* (2013.01);
(Continued)

(58) Field of Classification Search
None
See application file for complete search history.

(56) References Cited

U.S. PATENT DOCUMENTS

2004/0267152 A1  12/2004  Pineda
2005/0143589 A1*  6/2005  Donoghue .......... G06F 19/3412
552/650

(Continued)

FOREIGN PATENT DOCUMENTS

WO    WO 03/037231 A1    5/2003
WO    WO-2008/097201 A1  8/2008

OTHER PUBLICATIONS

Arvaneh et al., Optimizing EEG Channel Selection by Regularized Spatial Filtering and Multi Band Signal Decomposition, Proceedings of the 7th IASTED Intl. Conf. Biomedical Engineering, 86-90 (2010).

(Continued)

*Primary Examiner* — Etsub Berhanu
(74) *Attorney, Agent, or Firm* — Choate, Hall & Stewart LLP; Charles E. Lyon; Jeffrey S. Pelligrino

(57) ABSTRACT

A method of calibrating a motor imagery detection module and a system for motor rehabilitation are provided. The method comprises acquiring Electroencephalography (EEG) data from a subject; selecting classification features from the EEG data; wherein the feature selection comprises modelling an idle state $\omega_n$ of the subject by M sub-classes $\chi_j, j=1, \ldots, M$.

20 Claims, 12 Drawing Sheets

(51) Int. Cl.
  *A61B 5/0482* (2006.01)
  *A61B 5/00* (2006.01)
  *A61N 1/36* (2006.01)

(52) U.S. Cl.
  CPC ............. *A61B5/0482* (2013.01); *A61B 5/4205* (2013.01); *A61B 5/7267* (2013.01); *A61N 1/36003* (2013.01)

(56) References Cited

U.S. PATENT DOCUMENTS

| | | | | |
|---|---|---|---|---|
| 2006/0167371 | A1* | 7/2006 | Flaherty | A61F 2/50 600/545 |
| 2009/0048645 | A1* | 2/2009 | Philipp | A61N 1/3605 607/60 |
| 2009/0099627 | A1 | 4/2009 | Molnar et al. | |

OTHER PUBLICATIONS

Hamadicharef et al., Learning EEG-based Spectral-Spatial Patterns for Attention Level Measurement, IEEE International Symposium on Circuits and Systems (ISCAS), 1465-1468 (2009).

International Search Report for PCT/SG10/00127, 2 pages (issued Jan. 17, 2011).

Written Opinion for PCT/SG10/00127, 5 pages (issued Jan. 17, 2011).

International Search Report for PCT/SG11/00137, 5 pages (issued Aug. 20, 2011).

Written Opinion for PCT/SG11/00137, 7 pages (issued Aug. 20, 2011).

Singapore Written Opinion of 201207226-0, 5 pages (issued Aug. 29, 2013).

Ang, Kai Keng et al., Filter Bank Common Spatial Pattern (FBCSP) in Brain-Computer Interface, 2008 International Joint Conference on Neural Networks, 2390-2397 (2008).

Zhang, Dan et al., An Algorithm for Idle-State Detection in Motor-Imagery-Based Brain-Computer Interface, Computational Intelligence and Neuroscience, vol. 2007, Article ID 39714, 9 pages.

* cited by examiner

METHOD AND SYSTEM FOR MOTOR REHABILITATION

FIELD OF INVENTION

The present invention relates broadly to a method of calibrating a motor imagery detection module and to a system for motor rehabilitation.

BACKGROUND

Brain computer interfaces (BCIs) function as a direct communication pathway between a human brain and an external device. Furthermore, BCI systems can also provide an important test-bed for the development of mathematical methods and multi-channel signal processing to derive command signals from brain activities. As it directly uses the electrical signatures of the brain's activity for responding to external stimuli, it is particularly useful for paralyzed people who suffer from severe neuromuscular disorders and are hence unable to communicate through the normal neuromuscular pathway. The electroencephalogram (EEG) is one of the widely used techniques out of many existing brain signal measuring techniques due to its advantages such as its non-invasive nature and its low cost.

With regard to rehabilitation, currently, stroke rehabilitation commonly involves physical therapy by human therapists. Robotic rehabilitation may augment human therapists and enable novel rehabilitation exercises which may not be available from human therapists. Clinical trials involving brain-computer interface (BCI) based robotic rehabilitation are currently ongoing and some advantages over standard robotic rehabilitation include robotic assistance to the patient only if motor intent is detected and detection of motor intent being calibrated to patient-specific motor imagery electroencephalogram (EEG).

However, in addition to being at clinical trial level only, it is believed that current techniques are typically limited to rehabilitation of the limbs, i.e. arms and legs of a person.

Furthermore, to use EEG data for rehabilitation purposes, the EEG data is typically modeled into motor control data and idle state data. Typically, the idle state data are not separately modeled but rather, are modeled similarly to control data using a uni-modal approach. The approach is taken because modeling idle state data can be complex and difficult. One problem with the uni-modal approach is that false positive detections signalling control data may be received by a BCI system when a subject is instead in an idle state, e.g. not performing any mental control.

Therefore, there exists a need for a method of calibrating a motor imagery detection module and a system for motor rehabilitation that seek to address at least one of the above problems.

SUMMARY

In accordance with a first aspect of the present invention, there is provided a method of calibrating a motor imagery detection module, the method comprising acquiring Electroencephalography (EEG) data from a subject; selecting classification features from the EEG data; wherein the feature selection comprises modelling an idle state $\omega_n$ of the subject by M sub-classes $\chi_j$, j=1, ..., M.

Selecting the classification features may comprise computing a projection matrix for spatial filtering using multi-time segments for each of a plurality of frequency bands of the EEG data.

Selecting the classification features may further comprise computing candidate features of each frequency band.

Selecting the classification features may comprise computing mutual information of each candidate feature for each frequency band.

Selecting the classification features may comprise selecting, for each frequency band, the candidate features with maximum mutual information with motor imagery actions and rest respectively.

The method may further comprise training a non-linear regression model using the selected features.

The method may further comprise training a non-linear post-processing regression model using an output from the training of the non-linear regression model.

In accordance with a second aspect of the present invention, there is provided a method of motor rehabilitation, the method comprising extracting features from Electroencephalography (EEG) data of a subject, wherein the feature extraction comprises using a multi-modal model for an idle state $\omega_n$ of the subject including M subclasses $\chi_j$, j=1, ..., M; using a rehabilitation module to monitor an output of the multi-modal model for motor control signals; and if motor control signals are detected, applying functional electrical stimulation (FES) to the subject.

In accordance with a third aspect of the present invention, there is provided a system for motor imagery detection, the system comprising a processor capable of acquiring Electroencephalography (EEG) data from a subject; wherein the processor is further capable of selecting classification features from the EEG data; and further wherein the feature extraction comprises modelling an idle state $\omega_n$ of the subject by M sub-classes $\chi_j$, j=1, ..., M.

Selecting the classification features may comprise computing a projection matrix for spatial filtering using multi-time segments for each of a plurality of frequency bands of the EEG data.

Selecting the classification features may comprise computing mutual information of each candidate feature for each frequency band.

Selecting the classification features may comprise computing mutual information of each candidate feature for each frequency band.

Selecting the classification features may comprise selecting, for each frequency band, the candidate features with maximum mutual information with motor imagery actions and rest respectively.

The processor may be further capable of training a non-linear regression model using the selected features.

The processor may be further capable of training a non-linear post-processing regression model using an output from the training of the non-linear regression model.

In accordance with a fourth aspect of the present invention, there is provided a system for motor rehabilitation, the system comprising an input for acquiring Electroencephalography (EEG) data of a subject; a processor capable of extracting features from the EEG data using a multi-modal model for an idle state $\omega_n$ of the subject including M sub-classes $\chi_j$, j=1, ..., M; a rehabilitation module to monitor an output provided by the processor for motor control signals, the rehabilitation module capable of applying functional electrical stimulation (FES) to the subject.

In accordance with a fifth aspect of the present invention, there is provided a computer readable data storage medium having stored thereon computer code means for instructing a computer processor to execute a method of calibrating a motor imagery detection module of the first aspect.

In accordance with a sixth aspect of the present invention, there is provided a computer readable data storage medium having stored thereon computer code means for instructing a computer processor to execute a method of motor rehabilitation of the second aspect.

In accordance with a seventh aspect of the present invention, there is provided a method for brain-computer interface (BCI) based interaction, the method comprising the steps of acquiring a subject's EEG data; processing the EEG data to determine a motor imagery of the subject; detecting a swallow movement of the subject using a detection device; and providing feedback to the subject based on the motor imagery, the movement, or both; wherein providing the feedback comprises activating a stimulation element for providing a stimulus to throat muscles of the subject.

The method may comprise processing the EEG data to determine whether a specific swallow motor imagery is performed by the person; and activating the stimulation element if the specific swallow motor imagery is performed.

The feedback may further comprise a separate visual feedback to the person if the specific swallow motor imagery is performed.

The method may comprise determining whether a swallow movement is performed by the person; and activating the stimulation element if the swallow movement is performed.

The feedback may further comprise a separate visual feedback to the person if the swallow movement is performed.

The determining whether the swallow movement is performed by the subject may occur over a period of time.

The processing of the EEG data may comprise using a trained classification algorithm.

Training the classification algorithm may comprise dividing the EEG data into a plurality of segments, for each segment, dividing a corresponding EEG signal portion into a plurality of frequency bands, for each frequency band, computing a spatial filtering projection matrix based on a CSP algorithm and a corresponding feature, and computing mutual information of each corresponding feature with respect to one or more motor imagery classes; for each segment, summing the mutual information of all the corresponding with respect to the respective classes, and selecting the corresponding features of the segment with a maximum sum of mutual information for one class for training.

The method may further comprise training classifiers of the classification algorithm using the selected corresponding features.

Training the classifiers may comprise non-linear regression using the selected corresponding features and non-linear post-processing regression using an output from the non linear regression.

Computing the spatial filtering projection matrix based on the CSP algorithm may comprise using a multi-modal multi-time segment for each frequency band.

The multi-modal multi-time segment for each frequency band may comprise a multi-modal representation of idle states.

In accordance with a eighth aspect of the present invention, there is provided a brain-computer interface system comprising means for acquiring a subject's EEG data; means for processing the EEG data to determine a motor imagery of the subject; means for detecting a swallow movement of the subject using a detection device; and means for providing feedback to the subject based on the motor imagery, the movement, or both; wherein the means for providing the feedback comprises a stimulation element for providing a stimulus to the subject.

The stimulus may comprise functional electrical stimulation.

The system may further comprise a screen for providing visual feedback to the person based on the motor imagery, the movement, or both.

In accordance with a ninth aspect of the present invention, there is provided a computer readable data storage medium having stored thereon computer code means for instructing a computer processor to execute a method of brain-computer interface (BCI) based interaction of the seventh aspect.

BRIEF DESCRIPTION OF THE DRAWINGS

Embodiments of the invention will be better understood and readily apparent to one of ordinary skill in the art from the following written description, by way of example only, and in conjunction with the drawings, in which.

DETAILED DESCRIPTION

Figure 1:
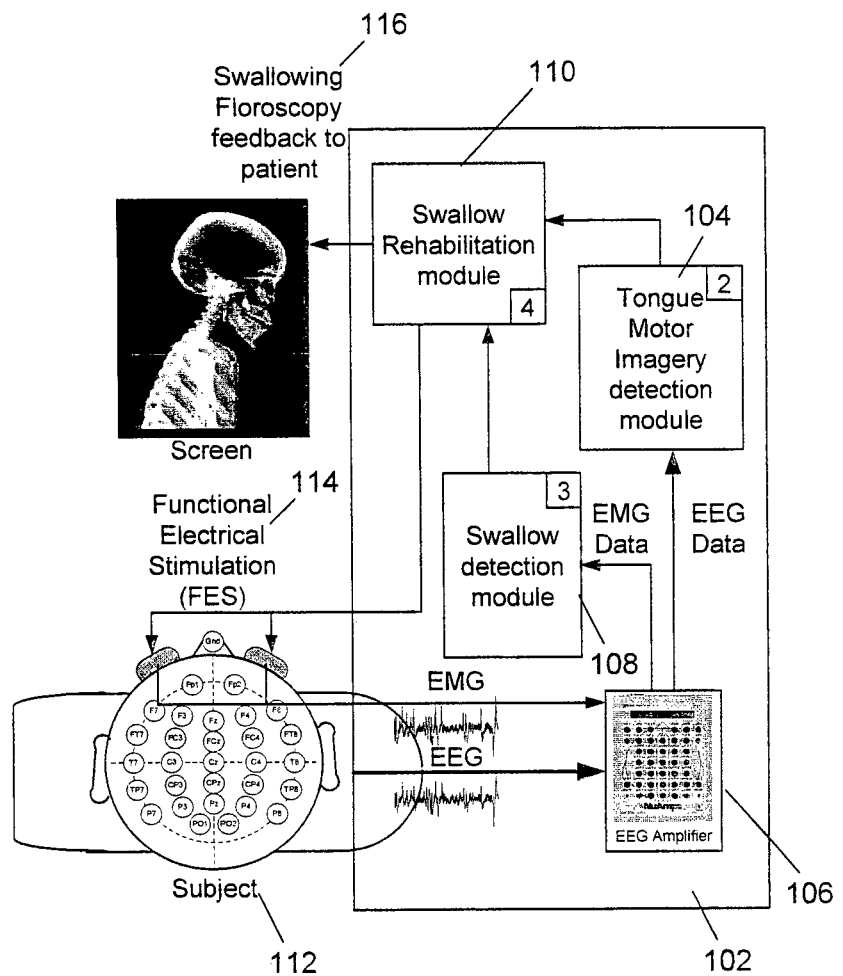
FIG. 1 is a schematic diagram illustrating a non-invasive Electroencephalography (EEG)-based brain-computer interface (BCI) system for stroke/swallow rehabilitation in an example embodiment.

Some portions of the description which follows are explicitly or implicitly presented in terms of algorithms and functional or symbolic representations of operations on data within a computer memory. These algorithmic descriptions and functional or symbolic representations are the means used by those skilled in the data processing arts to convey most effectively the substance of their work to others skilled in the art. An algorithm is here, and generally, conceived to be a self-consistent sequence of steps leading to a desired result.

The steps are those requiring physical manipulations of physical quantities, such as electrical, magnetic or optical signals capable of being stored, transferred, combined, compared, and otherwise manipulated.

Unless specifically stated otherwise, and as apparent from the following, it will be appreciated that throughout the present specification, discussions utilizing terms such as "scanning", "calculating", "determining", "replacing", "generating", "initializing", "outputting", or the like, refer to the action and processes of a computer system, or similar electronic device, that manipulates and transforms data represented as physical quantities within the computer system into other data similarly represented as physical quantities within the computer system or other information storage, transmission or display devices.

The present specification also discloses apparatus for performing the operations of the methods. Such apparatus may be specially constructed for the required purposes, or may comprise a general purpose computer or other device selectively activated or reconfigured by a computer program stored in the computer. The algorithms and displays presented herein are not inherently related to any particular computer or other apparatus. Various general purpose machines may be used with programs in accordance with the teachings herein. Alternatively, the construction of more specialized apparatus to perform the required method steps may be appropriate. The structure of a conventional general purpose computer will appear from the description below.

In addition, the present specification also implicitly discloses a computer program, in that it would be apparent to the person skilled in the art that the individual steps of the method described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the invention.

Furthermore, one or more of the steps of the computer program may be performed in parallel rather than sequentially. Such a computer program may be stored on any computer readable medium. The computer readable medium may include storage devices such as magnetic or optical disks, memory chips, or other storage devices suitable for interfacing with a general purpose computer. The computer readable medium may also include a hard-wired medium such as exemplified in the Internet system, or wireless medium such as exemplified in the GSM mobile telephone system. The computer program when loaded and executed on such a general-purpose computer effectively results in an apparatus that implements the steps of the preferred method.

The invention may also be implemented as hardware modules. More particular, in the hardware sense, a module is a functional hardware unit designed for use with other components or modules. For example, a module may be implemented using discrete electronic components, or it can form a portion of an entire electronic circuit such as an Application Specific Integrated Circuit (ASIC). Numerous other possibilities exist. Those skilled in the art will appreciate that the system can also be implemented as a combination of hardware and software modules.

FIG. 1 is a schematic diagram illustrating a non-invasive Electroencephalography (EEG)-based brain-computer interface (BCI) system 102 for stroke/swallow rehabilitation in an example embodiment.

The BCI system 102 comprises a tongue motor imagery detection module 104 coupled to a signal amplifier 106, a swallow detection module 108 coupled to the signal amplifier 106 and a swallow rehabilitation module 110 coupled to both the tongue motor imagery detection module 104 and the swallow detection module 108.

In the example embodiment, a subject 112 provides EEG data to the tongue motor imagery detection module 104 and, if available, EMG data to the swallow detection module 108. The swallow rehabilitation module 110 can provide swallow Functional Electrical Stimulation (FES) 114 and fluoroscopy feedback 116 to the subject 112.

If a swallow intent is detected at the swallow rehabilitation module 110, a fluoroscopy video 116 is presented as a feedback to the patient/subject 112. In addition, swallow FES 114 is triggered to stimulate the swallowing muscle groups of the patient/subject 112.

In the example embodiment, for patients or subjects with mild dysphagia, the swallow detection module 108 is also calibrated to detect subject-specific Electromyography (EMG) data of swallowing actions for patients with mild dysphagia.

Patients with mild dysphagia can perform weak swallowing, but not a proper swallowing action as compared to healthy subjects. The ability to perform weak swallowing allows calibration to be performed using EMG data collected from a patient with mild dysphagia.

Figure 2:
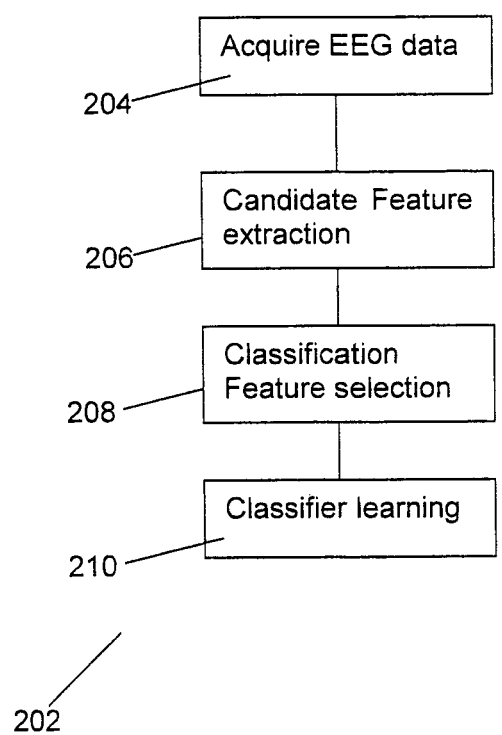
FIG. 2 is a schematic flowchart broadly illustrating calibration/construction of a tongue motor imagery detection module in an example embodiment.

FIG. 2 is a schematic flowchart 202 broadly illustrating calibration/construction of a tongue motor imagery detection module in an example embodiment. At step 204, EEG data is acquired from a subject. At step 206, candidate feature extraction is performed using the EEG data. At step 208, classification feature selection is performed based on the extracted features. At step 210, classifier learning is carried out.

The example embodiment can directly address significant inter-subject variability of motor imagery EEG by constructing a subject-specific motor imagery model. In the example embodiment, the EEG data is collected from the patient/subject in performing a number of motor imagery actions, for example, left hand, right hand, foot and tongue motor imageries.

Figure 3:
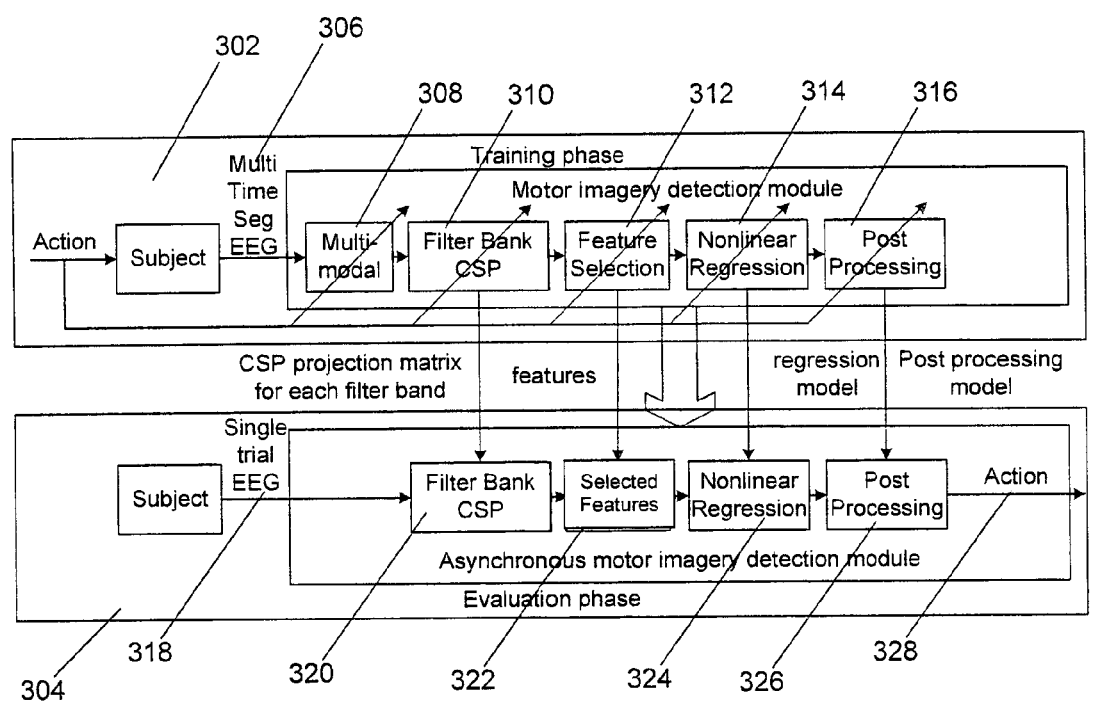
FIG. 3 is a schematic diagram showing a process of calibrating and using of a tongue motor imagery detection module in an example embodiment.

FIG. 3 is a schematic flow diagram illustrating the process of calibrating and using of a tongue motor imagery detection module in an example embodiment. The calibrating process is shown as training phase 302 and the use of the tongue motor imagery detection module is shown as evaluation phase 304.

At step 306, multi-time segment EEG data is obtained from a subject. At step 308, a multi-modal approach is taken for modeling control and idle states of the EEG data. At step 310, a filter bank Common Spatial Pattern (CSP) algorithm is used to extract CSP candidate features from each filter bank and time segment. At step 312, classification feature selection is performed. At step 314, nonlinear regression training is performed using the selected features. At step 316, post processing is performed.

At step 318, a single trial EEG is obtained from the subject. At step 320, the filter bank CSP algorithm is used for feature extraction from the EEG data of step 318. At step 322, selected features are obtained from the features extracted in step 320 based on the training at step 312. At step 324, nonlinear regression processing is performed on the selected features. At step 326, post processing is performed. At step 328, a motor intent output is provided.

The steps in FIG. 3 are described in more detail below.

The acquired EEG data (at step 306) is decomposed into multiple filter/frequency banks and time segments whereby the so-called Common Spatial Pattern (CSP) algorithm is employed to extract CSP features from each filter bank and time segment. An illustration of this process is provided later in FIG. 7.

The EEG data from each time segment and each filter bank can be linearly transformed using $$y = w^T x \qquad (1)$$

where x denotes an n×t matrix of the EEG data; y denotes an n×t matrix of uncorrelated sources; W denotes a n×n time-invariant transformation matrix; n is the number of channels; t is the number of EEG samples per channel; and $^T$ denotes a transpose operator. Further, $W = [w_1, w_2, \ldots, w_n]$ such that each $w_i$ represents a particular spatial filter.

Let the motor imagery state from a specific frequency band be denoted by $\omega_p$ and the idle state be denoted by $\omega_n$. Multiple motor imagery states from multiple frequency bands are considered later. Let the probability of the two states (i.e. motor imagery state and idle state) be respectively denoted by $P(\omega_p)$ and $P(\omega_n)$ such that $P(\omega_p) + P(\omega_n) = 1$, and the class conditional probability density functions be respectively denoted by $p(x|\omega_p)$ and $p(x|\omega_n)$ whereby x is a random sample of the EEG measurement. The so-called Bayes error for classifying x into the two classes is given by $$\varepsilon(x) = \int \min[P(\omega_p) p(x|\omega_p), P(\omega_n) p(x|\omega_n)] dx \qquad (2)$$

$$\equiv \int_{R_n} p(x|\omega_p) P(\omega_p) dx + \int_{R_p} p(x|\omega_n) P(\omega_n) dx$$

where $R_p$ is the Bayes decision region in which $p(x|\omega_p) P(\omega_p) > p(x|\omega_n) P(\omega_n)$, and $R_n$ is the Bayes decision region in which $p(x|\omega_n) P(\omega_n) > p(x|\omega_p) P(\omega_p)$.

The inventors have recognized that the close-form expression for the Bayes error cannot be obtained except in very special cases. Hence, in the example embodiment, the upper bound of the Bayes error is obtained instead. The Bhattacharyya bound of equation (2) is given by $$\epsilon_B(x) = \sqrt{P(\omega_p) P(\omega_n)} \int \sqrt{p(x|\omega_p) p(x|\omega_n)} dx \qquad (3)$$

The Bhattacharyya bound $\epsilon_B(y)$ is in the same form as equation (3) except that the variables and the probability density functions are replaced by y and its probability density functions. Therefore, the objective of linear spatial filtering can also be viewed as optimizing the linear projection matrix w to yield the minimal Bhattacharyya bound $\epsilon_B(y)$. Since the Bhattacharyya bound depends on the probability density functions, it can be treated under a uni-model or a multi-modal approach discussed separately in the following.

For the uni-model approach, let $p(x|\omega_p)$ and $p(x|\omega_n)$ be modeled by uni-modal Gaussian functions with covariance matrices $\psi_p$ and $\omega_n$ respectively. Further, it is assumed that the EEG data is band-pass filtered, in which the mean of both classes is assumed to be zero. The probability density functions can then be modeled as $$p(X|\omega_p) \sim N(0, \psi_p) \qquad (4)$$

$$\sim (2\pi)^{-\frac{n_c}{2}} |\psi_p|^{-\frac{1}{2}} \exp\left(-\frac{1}{2} X^T \psi_p^{-1} X\right)$$

and $$p(X|\omega_n) \sim (2\pi)^{-\frac{n_c}{2}} |\psi_n|^{-\frac{1}{2}} \exp\left(-\frac{1}{2} X^T \psi_n^{-1} X\right), \qquad (5)$$

where $n_c$ is the number of dimensions or channels of $\omega_p$ and $\omega_n$.

The Bhattacharyya bound is thus given by $$\varepsilon_H = \sqrt{P(\omega_p) P(\omega_n)} \exp\left(\frac{1}{2} \log \frac{\left|\frac{\psi_p + \psi_n}{2}\right|}{\sqrt{|\psi_p||\psi_n|}}\right), \qquad (6)$$

where |•| denotes the determinant of a square matrix.

The Bhattacharyya bound after spatial filtering using w can be written in a similar form by replacing the covariance matrices with that from the transformed data $\psi_p$ and $\psi_n$ using $\psi_p(y) = w^T \psi_p w$ and $\psi_n(y) = w^T \psi_n w$. The closed-form solution to minimizing the Bhattacharyya bound with respect to w can thus be obtained as follows. Given a particular selection of m, the optimum w is the collection of top m eigenvectors of $\psi_n^{-1} \psi_p$, or $$\psi_p w_i = \lambda_i \psi_n w_i, \qquad (7)$$

where $\lambda_i$ is the ith eigenvalue and $w_i$ the corresponding eigenvector. The eigenvectors obtained correspond to the common spatial pattern (CSP) algorithm that is typically used by motor imagery-based BCI systems to minimize the Bhattacharyya bound.

The inventors have recognized that the detection of the idle state in which the user/subject is at rest and not performing mental control may be crucial, to minimize false positive detections in an asynchronous BCI system. In the example embodiment, a multi-modal approach (compare step 308) of modeling the idle states in an asynchronous motor imagery-based BCI system is proposed, using the framework of the Bhattacharyya bound. By adopting the multi-modal approach, a number of problems of the uni-modal approach can be addressed.

Firstly, from a brain signal viewpoint, the idle state comprises multiple manifestations of all possible EEG patterns other than those that are associated with control motor imagery states. Since the user can be performing any mental activity other than those of the control motor imagery tasks during the idle state, the EEG measurements of the idle state is largely diversified in terms of spatio-spectral characteristics. Therefore, a multi-modal approach is more appropriate to model the idle state as compared to the uni-modal approach.

Secondly, from a linear transformation viewpoint, the optimum spatial filters that assume the uni-modal approach may fail to pick up discriminative spatial patterns.

An illustration of the difference between the multi-modal approach and the uni-modal approach is provided later in FIG. 8.

For the multi-modal approach of the example embodiment (compare step 308), let the idle state $\omega_n$ be modeled by M sub-classes $\chi_j$, $j = 1, \ldots, M$. Let the prior probability of each sub-class be denoted by $\tilde{P}(\chi_j)$ such that $\sum_{j=1}^{M} \tilde{P}(\chi_j) = 1$. Further, it is assumed that each sub-class is modeled by a Gaussian distribution function with zero-mean and a covariance matrix $\tilde{\psi}_j$. Hence, the distribution of the idle state $\omega_n$ can then be expressed as a Gaussian mixture model given by $$p(x|\omega_n) \sim \sum_{j=1}^{M} \tilde{p}(x_j) N(0, \tilde{\psi}_j) \qquad (8)$$

$$\sim (2\pi)^{-\frac{n_c}{2}} \sum_{j=1}^{M} \tilde{p}(x_j) |\tilde{\psi}_j|^{-\frac{1}{2}} \exp\left(-\frac{1}{2} X^T \tilde{\psi}_j^{-1} X\right)$$

After spatial filtering using the linear transformation W, the motor imagery states $P(\omega_p)$ and the idle state $P(\omega_n)$ are still Gaussian distributions. Hence, the distributions of the motor imagery states $P(\omega_p)$ and the idle state $P(\omega_n)$ can be expressed as $$p(y|\omega_p) \sim N(0, \psi_{p(y)}) \quad (9)$$

$$p(y|\omega_n) \sim \sum_{j=1}^{M} \tilde{p}(\chi_j) N(0, \tilde{\psi}_{j(y)}), \quad (10)$$

where $$\psi_{p(y)} = W^T \psi_p W, \quad (11)$$

$$\tilde{\psi}_{j(y)} = W^T \tilde{\psi}_j W, \quad (12)$$

and the Bhattacharyya bound is given by $$\epsilon_B(y) = \sqrt{P(\omega_p)P(\omega_n)} \int \sqrt{p(y|\omega_p)p(y|\omega_n)} dy. \quad (13)$$

The inventors have recognised that it can be difficult to compute the Bhattacharyya bound in equation (13). Hence, an approximate numerical solution is proposed. By ignoring the constant factor $\sqrt{P(\omega_p)P(\omega_n)}$, the Bhattacharyya coefficient that comprises the integral in equation (13) can be expressed as $$\mu = \int \sqrt{p(y|\omega_p)p(y|\omega_n)} \, dy \quad (14)$$

$$\equiv \int \mu_1(y)\mu_2(y) dy,$$

where $\mu_1(y) = \sqrt{p(y|\omega_p)}$ and $\mu_2(y) = \sqrt{p(y|\omega_n)}$.

By expanding $\mu_1(y)$ in a form that is similar to equation (5), $$\mu_1(y) = \sqrt{(2\pi)^{-\frac{n_c}{2}} |\psi_{p(y)}|^{-\frac{1}{2}} \exp\left(-\frac{1}{2} y^T \psi_{p(y)}^{-1} y\right)} \quad (15)$$

$$= \left\{ (2\pi)^{-\frac{n_c}{2}} |2\psi_{p(y)}|^{-\frac{1}{2}} \exp\left(-\frac{1}{2} y^T (2\psi_{p(y)})^{-1} y\right) \right\} \cdot$$

$$\left\{ (2\pi)^{\frac{n_c}{4}} 2^{\frac{n_c}{2}} |\psi_{p(y)}|^{\frac{1}{4}} \right\}$$

The expression in the first curly bracket of equation (15) can be viewed as a probability density function $$P(y) = N(0, 2\psi_{p(y)}), \quad (16)$$

and the expression in the second curly bracket of equation (15) can be written with $\mu_2(y)$ as $$Q(y) = (2\pi)^{\frac{n_c}{4}} 2^{\frac{n_c}{2}} |\psi_{p(y)}|^{\frac{1}{4}} \cdot \sqrt{\sum_{j=1}^{M} \tilde{P}(\chi_j) N(0, \tilde{\psi}_{j(y)})}. \quad (17)$$

Therefore, the Bhattacharyya coefficient can be expressed as $$\mu = \int P(y) Q(y) dy. \quad (18)$$

Since $P(y)$ is a probability distribution function, the Bhattacharyya coefficient can be expressed as the expectation of Q given by $$\mu = E[Q(y)], \quad (19)$$

where $$p(y|\omega_p) \sim N(0, 2W^T \psi_p W) \quad (20)$$

The variable y in equation (20) is obtained by transforming the variable x in the original space using w whereby $$p(\chi|\omega_p) \sim N(0, 2\psi_p). \quad (21)$$

It is assumed that $p(\chi_i|\omega_p) \sim N(0, \psi_p)$, $i=1, \ldots, n_p$ where $n_p$ denotes the number of trials of EEG of the motor imagery state $\psi_p$ from equation (5).

Hence, to have $\hat{x}$ that follows the distribution in equation (21), $$p(\sqrt{2}\hat{x}_i|\omega_p) \sim N(0, 2\psi_p), i = \ldots, n_p, \quad (22)$$

and therefore $$\mu = \lim_{n_p \to \infty} \frac{1}{n_p} \sum_{i=1}^{n_p} Q(W^T \sqrt{2}\, \hat{x}_i) \quad (23)$$

The inventors have recognized that equation (23) is a complex function over w while the global optimum is also difficult to achieve. Hence, in the example embodiment, the inventors propose a simplified problem of searching for the optimum w among a given set of candidates.

Firstly, let the candidate set be $K_{cand}$ which comprises $n_{cand}$ vectors. Further consider a subset K that contains $n_{sel}$ selected vectors. A transformation matrix formed by the subset K is then $w_K$. The problem is then formulated to search for the optimum set $K_{opt}$ that satisfies $$K_{opt} = \underset{K}{\operatorname{argmin}} \frac{1}{n_p} \sum_{i=1}^{n_p} Q(W_K^T \sqrt{2}\, \hat{x}_i) \quad (24)$$

In the example embodiment, a small $K_{cand}$ is considered so that it is computationally feasible to enumerate all possible combinations of selecting $n_{sel}$ from $n_{cand}$. The following algorithm is proposed to obtain $K_{cand}$ and $K_{opt}$. At a first step, let $K_{cand} = \emptyset$. At a second step, for each idle state subclass m, compute projection matrices $w_m$ that maximizes the Bhattacharyya distance between the idle state subclass m and the motor imagery class, by solving the eigen problem given in equation (7). Thereafter, select from $w_m$ the linear projection vectors which produce the least Bhattacharyya coefficient $$\lambda_i + \frac{1}{\lambda_i} \quad (25)$$

where $\lambda_i$ is the eigen value. The set of selected vectors from $w_m$ for the idle state m is then denoted as $K_m$. Next, let $K_{cand} \cup K_m \to K_{cand}$. At a third step, enumerate all $n_{sel}$-sized subsets of $K_{cand}$, and compute the estimate of Bhattacharyya coefficient using equation (23) for each subset. At a fourth step, select the subset $K_{opt}$ which satisfies equation (24).

At step 310, the optimal transformation W obtained from the multi-modal approach is then integrated into a modified version of the so-called Filter Bank Common Spatial Pattern algorithm (FBCSP) (Ang et. al., 2008, IJCNN'08, 2391-2398) that deals with multiple classes which involve multiple motor imagery classes and a single idle state class, as well as multiple frequency bands for motor imagery detection. The FBCSP has been modified for use in the example embodiment such that it can be used with a plurality of idle state subclasses for a multi-modal approach for modeling the idle states.

In the example embodiment, the variances of a small number m of the spatial filtered signal Z(t) obtained by the CSP algorithm are used as features. The signal $Z_p(t)$, $p \in \{1 \ldots 2m\}$ that maximizes the difference in the variance of the two classes of EEG data are associated with the largest eigenvalues $\lambda$ and $(1-\lambda)$. These signals, for each time segment and each filter bank, are used to form a feature vector $X_p$ for each time segment and each filter bank.

$$X_p = \log\left(\text{var}(Z_p(t)) \bigg/ \sum_{i=1}^{2m} \text{var}(Z_p(t))\right) \quad (26)$$

At step 312, feature selection is performed using Mutual Information. Assuming a total of d features from each time segment $F=\{f_1, f_2, \ldots f_d\}$, the Mutual Information $1(f_i; \Omega)$ $\forall i=1 \ldots d$, $f_i \in F$ of each feature from all the time segments and all the filter banks is computed with respect to the class $\Omega$. Thereafter, a set of $k=4$ features is selected from each time segment that maximizes $I(f_i; \Omega)$ using $$F = F \setminus \{f_i\}, S = \{f_i\} \mid I(f_i; \Omega) = \max_{j=1 \ldots d, f_j \in F} I(f_j; \Omega). \quad (27)$$

The mutual information of all the features from each time segment are then summed together. The time segment with the maximum sum of mutual information is then selected.

The CSP projection matrix W from the selected time segment and the selected frequency band features are retained. At step 314, non-linear regression training is carried out using the selected features. The extracted features from all the trials belonging to the selected time segment are retained as training features for the non-linear regression while the features from the non selected time segments are dropped. The selected features are then linearly normalized to the range [−1 1] using the upper and lower bounds of the training set features. To map the features to the desired outputs, a generalized regression neural network (GRNN) is used. The desired outputs refer to instructions given to the subject in the training phase 302, such as performing motor imagery or idling/rest. The neural network comprises two layers of neurons. The first layer comprises radial basis function neurons, while the second layer comprises linear neurons with normalized inputs.

At step 316, post processing training is carried out. Another GRNN is used to perform the post-processing. The input of the neural network is a window of predicted labels obtained from the non-linear regression of step 314, while the output is the desired output.

Figure 4:
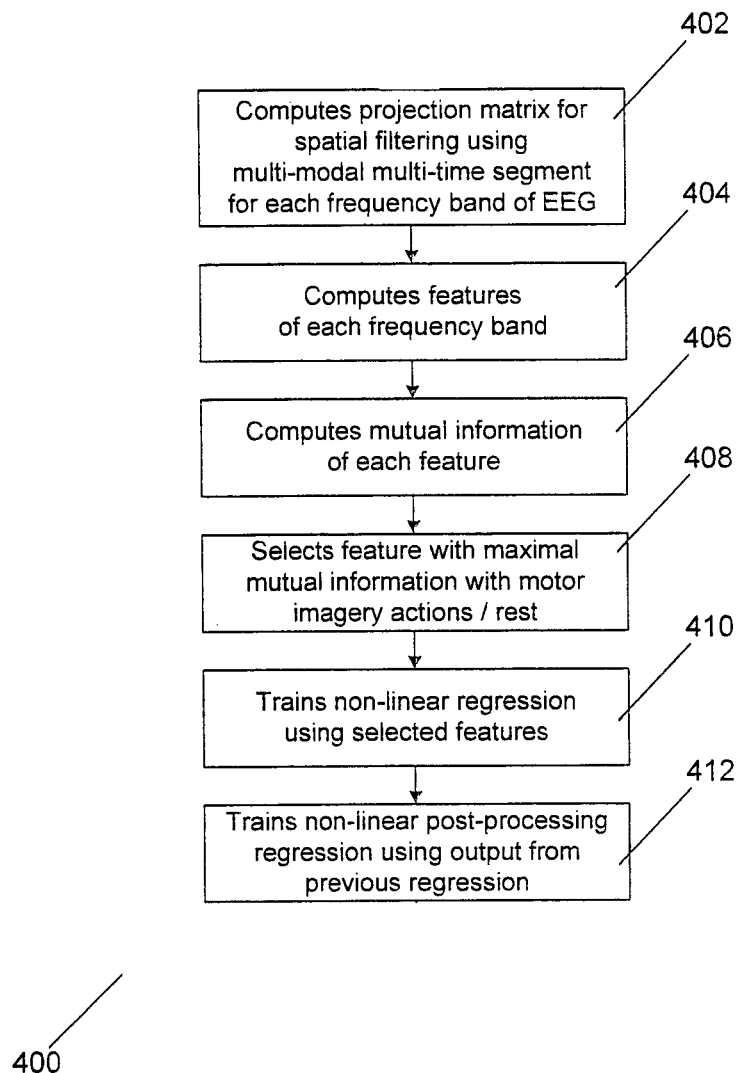
FIG. 4 is a schematic flowchart illustrating a calibration process of a motor imagery detection module in an example embodiment.

FIG. 4 is a schematic flowchart 400 summarising a calibration process of a motor imagery detection module in an example embodiment. At step 402, a projection matrix is computed for spatial filtering using multi-modal multi-time segments for each of a plurality of frequency bands of EEG data. At step 404, candidate features of each frequency band are computed. At step 406, mutual information of each feature of each frequency band are computed. At step 408, candidate features with maximum mutual information with motor imagery action and rest states respectively are selected for each frequency band where applicable. It is appreciated that not all frequency bands can yield candidate features. At step 410, non-linear regression training is carried out using the selected features. At step 412, non-linear post-processing regression training is carried out using output from step 410.

In the example embodiment, after calibration of the tongue motor imagery detection module, rehabilitation can be performed for severe and mild dysphagias.

For example, for severe and mild dysphagias, the swallow rehabilitation module 110 (FIG. 1) employs the calibrated subject-specific tongue motor imagery detection module 104 (FIG. 1) and one or more muscle activation detection modules, such as the swallow detection module 108 (FIG. 1), to perform real time muscle activation detection of the level of swallow intent of the patient/subject 112 (FIG. 1). In an alternative example embodiment, the swallow detection module 108 (FIG. 1) can be used to perform both motor imagery detection (using EEG data) and muscle activation detection (using EMG data).

Turning back to FIG. 3, after the training phase 302, the evaluation phase 304 is started. Based on the features selected at step 312 during the calibration phase 302, spatial filtering is then performed at step 320 using the projection matrix W on the acquired EEG data from step 318. At step 322, using the feature selection performed in step 312 which selects relevant features among all the features using the training data in phase 302, these selected features are "included" in step 322 from the features extracted in step 320 for further processing, and non-selected features are "excluded". The trained non-linear regression and post processing using GRNN from steps 314 and 316 respectively are then used (at steps 324, 326 respectively) to compute the asynchronous motor intent output at step 328.

Referring to FIG. 1, the calibration of the swallow detection module 108 is substantially identical to the calibration of the tongue motor imagery detection module 104 except that instead of performing the calibration based on the EEG data collected from the patient in performing motor imageries of tongue (as is done for the tongue motor imagery detection module 104), the calibration of the swallow detection module 108 is performed based on EMG data collected from the patient in performing tongue movement and swallowing of e.g. drinking water.

Furthermore, the calibration process of the tongue motor imagery detection module 104 comprises spatial filtering and temporal filtering of EEG data obtained from the subject. The calibration process for the swallow detection module 108 is similar to the process shown in FIG. 3 for calibrating the tongue motor imagery detection module 104. However, the calibration process of the swallow detection module 108 differs from FIG. 3 in the following ways. It is recognized that the signal to noise ratio of EMG data is generally larger than EEG data, and the EMG data comprises relatively less number of channels compared to the EEG data. This implies that the spatial information in the EMG data may not differ significantly from subject to subject. Hence, the EMG data of healthy subjects, not the patient, is used to calibrate the spatial filtering (compare step 310). Further, it is recognized that the temporal information in the EMG data may differ significantly from subject-to-subject. Hence, the EMG data of the patient is then used to calibrate the temporal filtering of the EMG data (compare step 312). That is, the inventors have recognized that the calibration of the swallow detection module 108 is performed jointly using the EMG data of healthy subjects and of the patient because the patient can only perform weak swallowing whereas healthy subjects can perform proper swallowing. Since EMG data can contain subject-specific frequency components, the temporal filtering is calibrated using the patient's EMG data.

Referring to the Functional Electrical Stimulation (FES), swallowing can be artificially induced by applying FES to the pharyngeal muscles of the subject. For healthy persons, swallowing can be done immediately at will. However, stroke victims with dysphagia may have issues with swallow initiations. In the system 102, swallow rehabilitation can be triggered by the swallow rehabilitation module 110. FES for swallowing is controlled by a hybrid bio-signal control system, that is, the patient's swallow intention is captured from EEG data if the patient is not able to perform any voluntary swallowing for severe dysphagia, or from both the EEG data and EMG data if the patient is weak in performing swallowing for mild dysphagia. In the example embodiment, using both EEG and EMG is more effective because the inventors have recognized that detection of voluntary swallow intentions from EEG data is typically slower than from EMG data. Therefore, if the patient is weak in swallowing, the detection from the swallow intent from EMG data can be faster than from EEG data.

Figure 5:
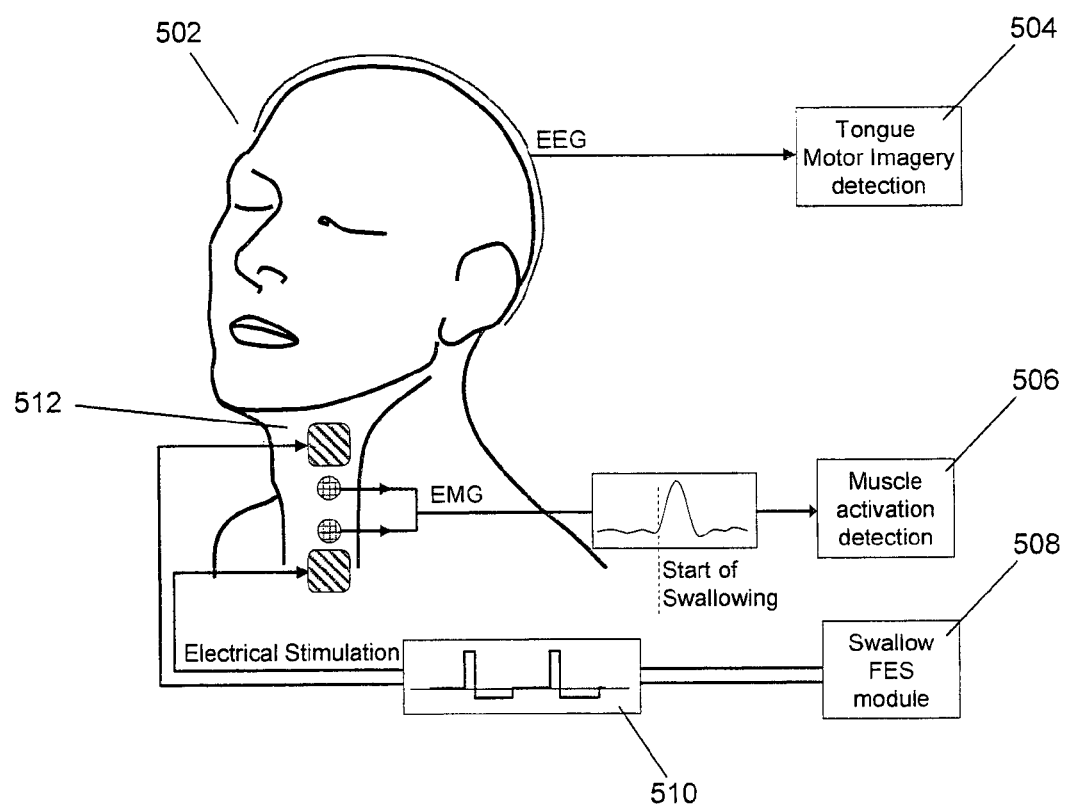
FIG. 5 is a schematic diagram illustrating use of both EEG data and Electromyography (EMG) data to provide functional electrical stimulation (FES) to a subject in an example embodiment.

FIG. 5 is a schematic diagram illustrating use of both EEG data and EMG data to provide FES to a subject in an example embodiment. In the figure, the subject 502 provides EEG data for tongue motor imagery detection 504. The subject can also provide EMG data for muscle activation detection 506. Based on the tongue motor imagery detection 504 and muscle activation detection 506, a swallow FES module 508 can detect a swallowing intention and provide electrical stimulation 510 to muscles located at the subject's 502 throat 512.

Table 1 tabulates the logic decisions in activating swallow rehabilitation for severe dysphagia. When the EEG data indicate that the patient/subject has a swallowing intention, e.g. the tongue motor imagery score is equal or more than a set threshold value determined by a rehabilitation therapist, swallow rehabilitation is activated (e.g. FES is provided).

TABLE 1

| EMG | EEG | Swallow Rehab |
|---|---|---|
| Don't care | Tongue motor imagery score < Therapist set threshold | Idle |
| Don't care | Tongue motor imagery score ≥ Therapist set threshold | Activate |

Table 2 tabulates the logic decisions in activating swallow rehabilitation for mild dysphagia. The swallow rehabilitation is only be activated when both the scores of the tongue motor imagery and swallowing EMG are above respective set threshold values determined by the rehabilitation therapist.

TABLE 2

| EMG | EEG | Swallow Rehab |
|---|---|---|
| Swallowing score < Therapist set threshold | Tongue motor imagery score < Therapist set threshold | Idle |
| Swallowing score < Therapist set threshold | Tongue motor imagery score ≥ Therapist set threshold | Idle |
| Swallowing score ≥ therapist set threshold | Tongue motor imagery score < Therapist set threshold | Idle |
| Swallowing score ≥ therapist set threshold | Tongue motor imagery score ≥ Therapist set threshold | Activate |

The thresholds in Tables 1 and 2 allow a therapist to progressively increase the difficulty of the rehabilitation therapy in order to cater for patients with different speeds of progress in their therapy.

Figure 6:
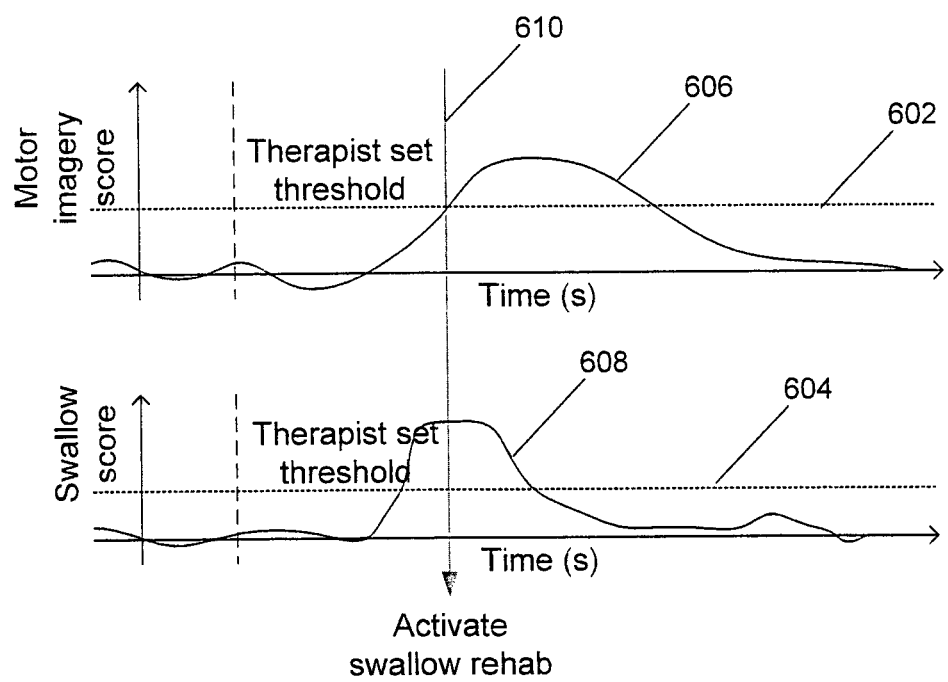
FIG. 6 is a schematic diagram illustrating a trigger for activating swallow rehabilitation for mild dysphagia in an example embodiment.

FIG. 6 is a schematic diagram illustrating a trigger for activating swallow rehabilitation for mild dysphagia in an example embodiment 602 indicates the threshold value set by a therapist for a motor imagery score and 604 indicates the threshold value set by a therapist for a swallow score. When both the motor imagery score 606 and the swallow score 608 of a patient are above their respective threshold values 602, 604, swallow rehabilitation is activated at time 610.

In the example embodiment, once swallow rehabilitation is activated, FES is applied to the subject/patient to stimulate the muscle groups responsible for the swallowing action for physiological feedback. A screen showing the fluoroscopy (compare 116 of FIG. 1) is also displayed for psychological feedback to the patient.

Figure 7:
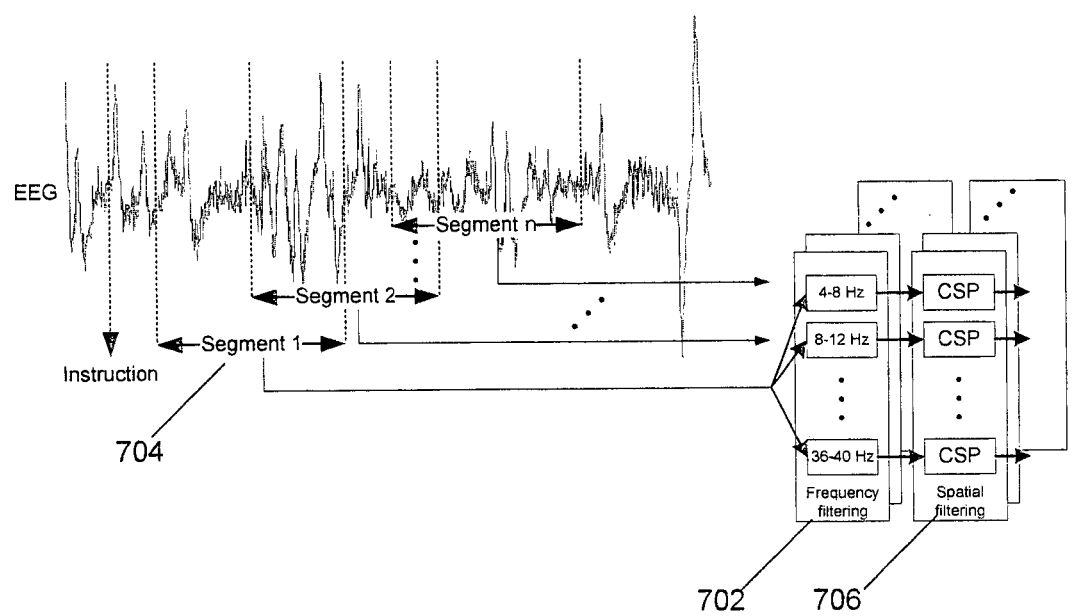
FIG. 7 is a schematic diagram showing decomposition of EEG data into multi time segments and frequency banks in an example embodiment.

FIG. 7 is a schematic diagram showing decomposition of EEG data into multi time segments and frequency banks in an example embodiment. Acquired EEG data is decomposed into multiple filter/frequency banks e.g. 702 and time segments e.g. 704 whereby the so-called Common Spatial Pattern (CSP) algorithm is employed to extract CSP features (compare 706) from each filter bank and time segment.

Figure 8:
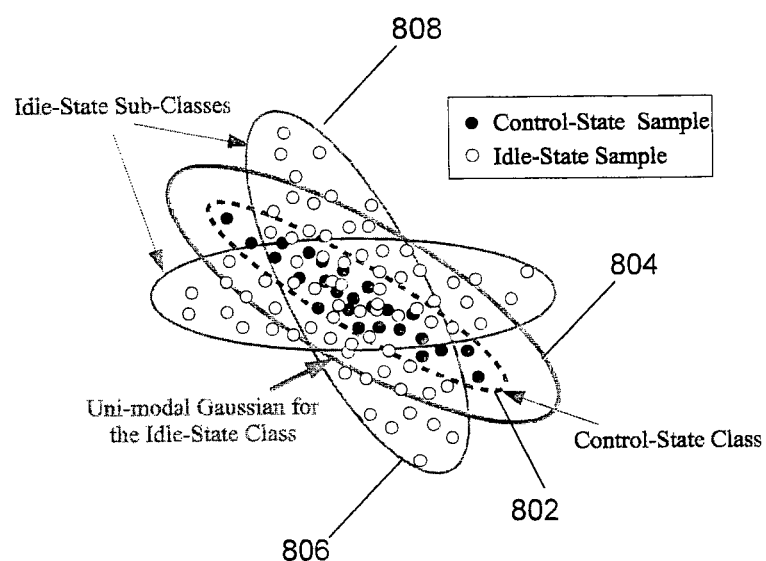
FIG. 8 is a schematic diagram illustrating a difference between a uni-modal approach and a multi-modal approach in modeling idle states.

FIG. 8 is a schematic diagram illustrating a difference between a uni-modal approach and a multi-modal approach in modeling idle states. The motor control-state class of samples/data (represented by the shaded dots) are in the Gaussian distribution 802. Using the uni-modal approach, a Gaussian distribution 804 is formed for the idle-state class of samples (represented by the unshaded dots). It can be seen that a plurality of the idle-state samples lie outside the distribution 804 which is undesirable in modeling. That is, the idle state distribution 804 modeled by using the uni-modal approach does not show a distinct spatial component that separates it from the control state distribution 802. In contrast, using the multi-modal approach of the example embodiment, two idle-state subclasses distributions 806, 808 are modelled to more accurately represent the idle-state samples. Each of the two idle state subclasses distributions 806, 808 has a distinct principal axis from the control state distribution 802. Thus, it can be seen that using the uni-modal approach results in an idle state distribution 804 that is too similar to the control state distribution 802 while using the multi-modal approach, two idle state subclasses distributions 806, 808 exhibiting distinguishing spatial directions that are different from the control state distribution 802 can be obtained to more accurately model the idle-state samples.

Table 3 shows experimental results performed to detect swallowing of fluid from tongue movement for mild dysphagia. The experiment is performed to classify EMG data of two healthy subjects (Subject 1 and Subject 2). Using a total of 4 EMG channels (2 left, 2 right) and 1 ground connection, 20 trials of each task are collected. The accuracies of classifying swallowing of fluid and tongue movement from EMG data are computed using 10×10-fold cross-validations on 2 different segment lengths/time (i.e. 1 and 2 s) For example, for a 2 second segment for Subject 2, the accuracy is 100%.

TABLE 3

| Length | Subject 1 | Subject 2 |
|---|---|---|
| 2 s | 96.75 | 100.00 |
| 1 s | 91.50 | 99.50 |

Figure 9:
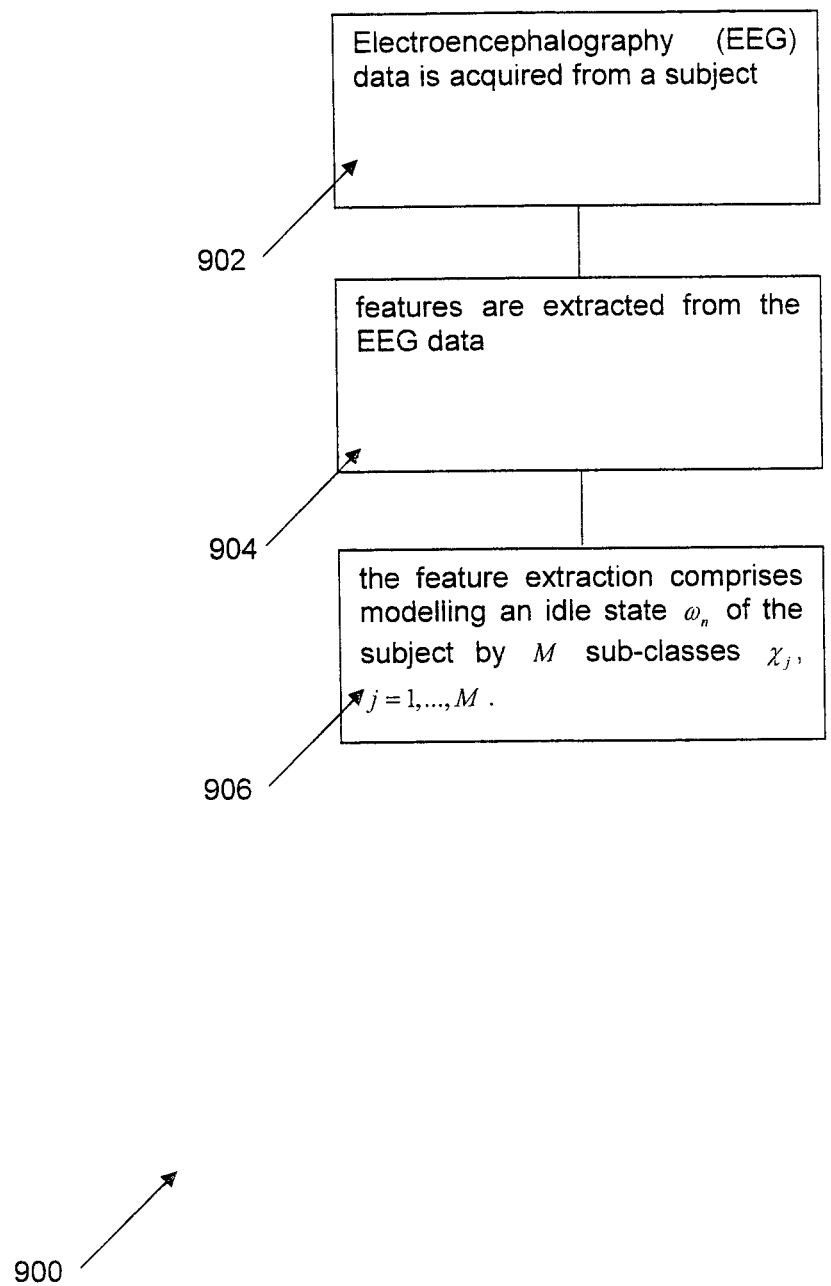
FIG. 9 is a schematic flowchart illustrating a method of calibrating a motor imagery detection module in an example embodiment

FIG. 9 is a schematic flowchart 900 illustrating a method of calibrating a motor imagery detection module in an example embodiment. At step 902, Electroencephalography (EEG) data is acquired from a subject. At step 904, features are extracted from the EEG data. At step 906, the feature extraction comprises modelling an idle state $\omega_n$ of the subject by M sub-classes $\chi_j$, j=1, . . . , M.

Figure 10:
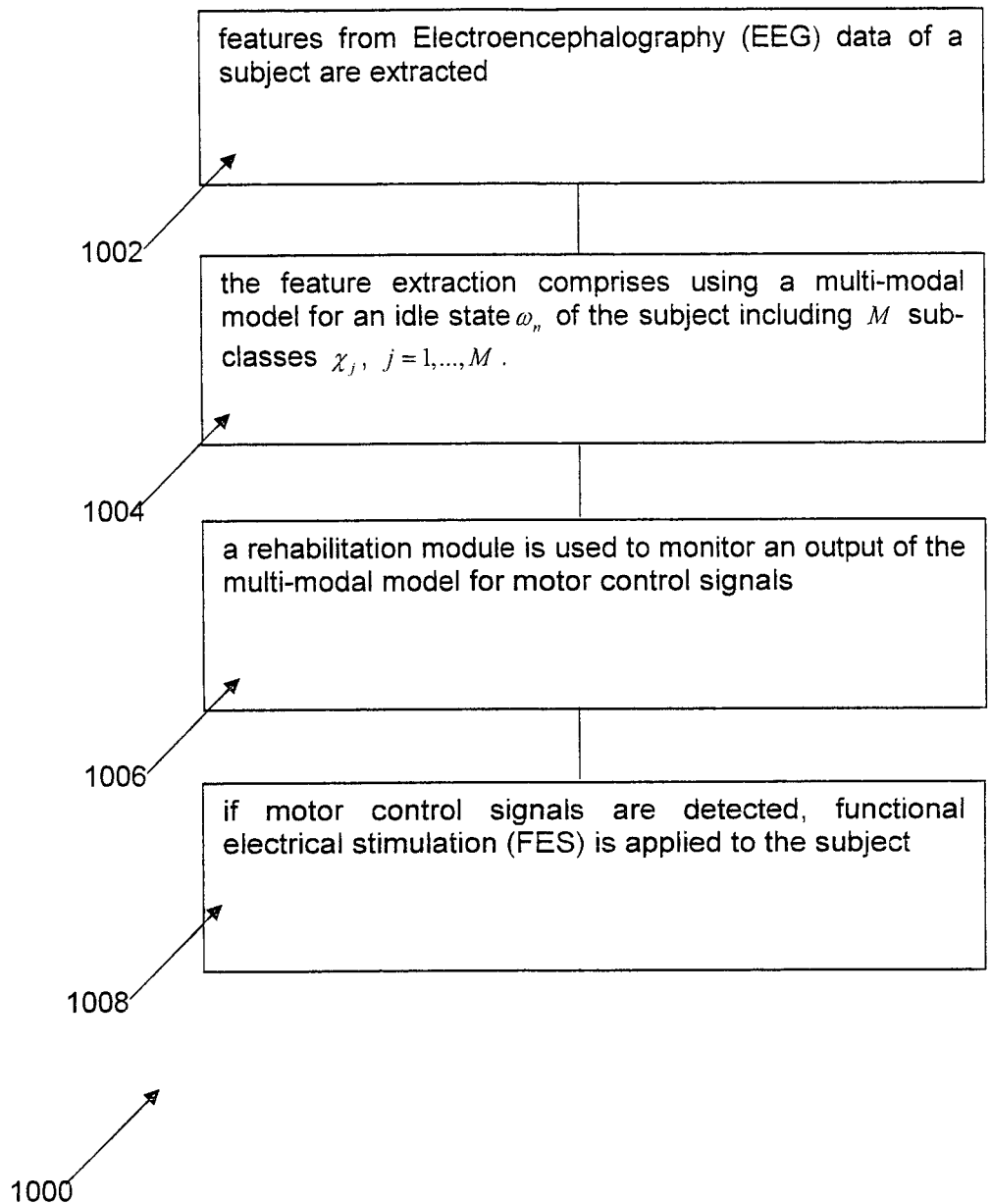
FIG. 10 is a schematic flowchart illustrating a method of motor rehabilitation in an example embodiment.

FIG. 10 is a schematic flowchart 1000 illustrating a method of motor rehabilitation in an example embodiment. At step 1002, features from Electroencephalography (EEG) data of a subject are extracted. At step 1004, the feature extraction comprises using a multi-modal model for an idle state $\omega_n$ of the subject including M sub-classes $\chi_j$, j=1, . . . , M. At step 1006, a rehabilitation module is used to monitor an output of the multi-modal model for motor control signals. At step 1008, if motor control signals are detected, functional electrical stimulation (FES) is applied to the subject.

Figure 11:
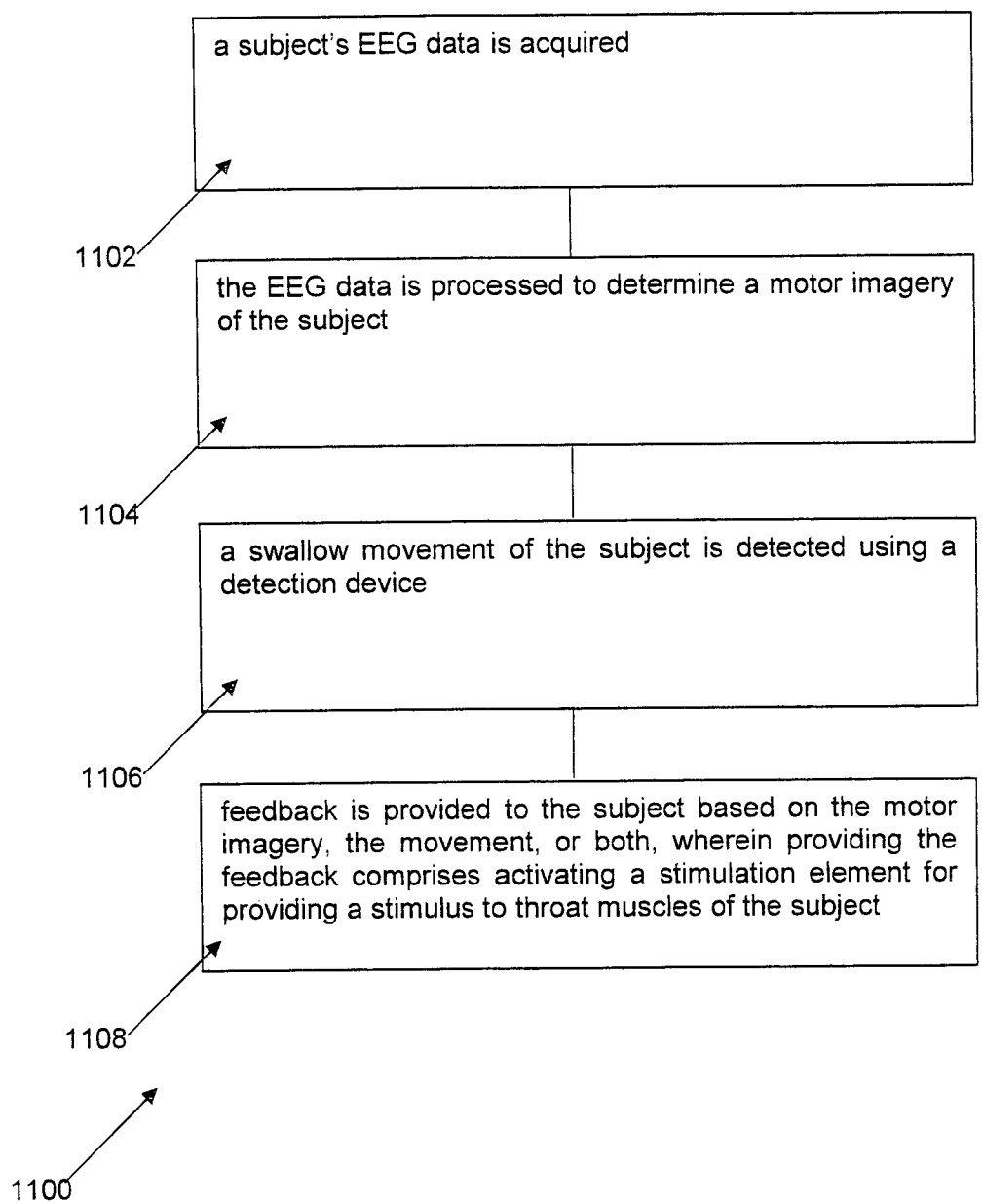
FIG. 11 is a schematic flowchart for illustrating a method for brain-computer interface (BCI) based interaction in an example embodiment.

FIG. 11 is a schematic flowchart 1100 for illustrating a method for brain-computer interface (BCI) based interaction in an example embodiment. At step 1102, a subject's EEG data is acquired. At step 1104, the EEG data is processed to determine a motor imagery of the subject. At step 1106, a swallow movement of the subject is detected using a detection device. At step 1108, feedback is provided to the subject based on the motor imagery, the movement, or both, wherein providing the feedback comprises activating a stimulation element for providing a stimulus to throat muscles of the subject.

Figure 12:
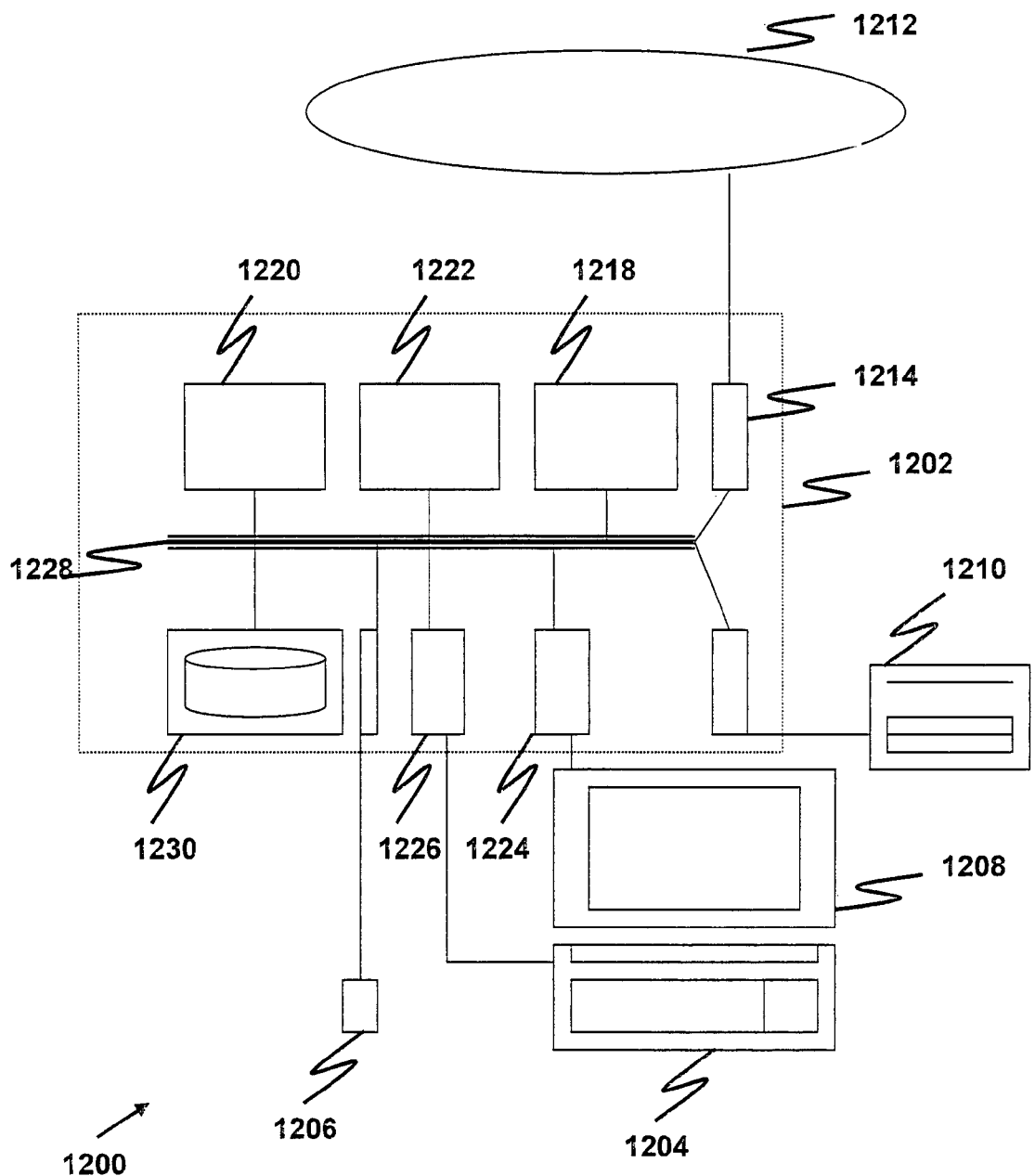
FIG. 12 is a schematic illustration of a computer system for implementing a method and system of calibrating a motor imagery detection module and/or of motor rehabilitation in an example embodiment.

The method and system of the described example embodiments can be implemented on a computer system 1200, schematically shown in FIG. 12. It may be implemented as software, such as a computer program being executed within the computer system 1200, and instructing the computer system 1200 to conduct the method of the example embodiments.

The computer system 1200 comprises a computer module 1202, input modules such as a keyboard 1204 and mouse 1206 and a plurality of output devices such as a display 1208, and printer 1210.

The computer module 1202 is connected to a computer network 1212 via a suitable transceiver device 1214, to enable access to e.g. the Internet or other network systems such as Local Area Network (LAN) or Wide Area Network (WAN).

The computer module 1202 in the example includes a processor 1218, a Random Access Memory (RAM) 1220 and a Read Only Memory (ROM) 1222. The computer module 1202 also includes a number of Input/Output (I/O) interfaces, for example I/O interface 1224 to the display 1208, and I/O interface 1226 to the keyboard 1204.

The components of the computer module 1202 typically communicate via an interconnected bus 1228 and in a manner known to the person skilled in the relevant art.

The application program is typically supplied to the user of the computer system 1200 encoded on a data storage medium such as a CD-ROM or flash memory carrier and read utilising a corresponding data storage medium drive of a data storage device 1230. The application program is read and controlled in its execution by the processor 1218. Intermediate storage of program data maybe accomplished using RAM 1220.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

The invention claimed is:

1. A method of calibrating a motor imagery detection module, the method comprising,
    acquiring Electroencephalography (EEG) data from a subject;
    decomposing the acquired EEG data into a plurality of frequency and time segment components;
    computing a projection matrix for spatial filtering for each of the plurality of frequency and time segment components;
    selecting classification features from the plurality of frequency and time segment components; and
    calibrating the motor imagery detection module using the selected classification features,
    wherein the feature selection comprises using a multi-modal model for an idle state $\omega_n$ of the subject including M sub-classes $\chi_j$, j=1, . . . , M.

2. The method as claimed in claim 1, wherein selecting the classification features further comprises computing candidate features of each of the plurality of frequency and time segment components.

3. The method as claimed in claim 2, wherein selecting the classification features comprises computing mutual information of each candidate feature for each of the plurality of frequency and time segment components.

4. The method as claimed in claim 3, wherein selecting the classification features comprises selecting, for each of the plurality of frequency and time segment components, the candidate features with maximum mutual information with motor imagery actions and rest respectively.

5. The method as claimed in claim 4, further comprising training a non-linear regression model using the selected classification features.

6. A method of motor rehabilitation, the method comprising, extracting features from Electroencephalography (EEG) data of a subject, wherein the feature extraction comprises using a multi-modal model for an idle state $\omega_n$ of the subject including M sub-classes $\chi_j$, j=1, . . . , M;
    using a rehabilitation module to monitor an output of the multi-modal model to detect motor control signals from the extracted features;
    and if motor control signals are detected,
    applying functional electrical stimulation (FES) to the subject.

7. A system for motor imagery detection, the system comprising,
    a signal amplifier capable of acquiring Electroencephalography (EEG) data from a subject, and
    a detection module for detecting motor imagery based on the EEG data received from the signal amplifier;
    wherein the detection module is configured to decompose the acquired EEG data into a plurality of frequency and time segment components, compute a projection matrix for spatial filtering for each of the plurality of frequency and time segment components, and select classification features from the plurality of frequency and time segment components; and
    wherein the feature selection comprises using a multi-modal modelling for an idle state $\omega_n$ of the subject including M sub-classes $\chi_j$, j=1, . . . , M.

8. The system as claimed in claim 7, wherein selecting the classification features further comprises computing candidate features of each of the plurality of frequency and time segment components and further comprises computing mutual information of each candidate feature for each of the plurality of frequency and time segment components.

9. The system as claimed in claim 8, wherein selecting the classification features comprises selecting, for each of the plurality of frequency and time segment components, the candidate features with maximum mutual information with motor imagery actions and rest respectively.

10. The system as claimed in claim 9, wherein the detection module is further configured to train a non-linear regression model using the selected classification features.

11. A non-transitory computer readable data storage medium having stored thereon computer code means for instructing a computer processor to execute a method of calibrating a motor imagery detection module as claimed in claim 1.

12. A method for brain-computer interface (BCI) based interaction, the method comprising the steps of:
    acquiring a subject's EEG data;
    processing the EEG data to determine a motor imagery of the subject;
    detecting a swallow movement of the subject using a detection device; and
    providing feedback to the subject based on the motor imagery, the movement, or both;
    wherein providing the feedback comprises activating a stimulation element for providing a stimulus to throat muscles of the subject, and
    wherein the processing of the EEG data comprises selecting classification features from the EEG data, and wherein the feature selection comprises using a multi-modal model for an idle state $\omega_n$ of the subject including M sub-classes $\chi_j$.

13. The method as claimed in claim 12, comprising:
    processing the EEG data to determine whether a specific swallow motor imagery is performed by the subject; and
    activating the stimulation element if the specific swallow motor imagery is performed.

14. The method as claimed in claim 13, wherein the feedback further comprises a separate visual feedback to the subject if the specific swallow motor imagery is performed.

15. The method as claimed in claim 12, wherein the processing of the EEG data comprises using a trained classification algorithm for said selecting the features from the EEG data.

16. The method as claimed in claim 15, further comprising training the classification algorithm, wherein training the classification algorithm comprises:
    dividing the EEG data into a plurality of segments,
    for each segment, dividing a corresponding EEG signal portion into a plurality of frequency bands,
    for each frequency band, computing a spatial filtering projection matrix based on a Common Spatial Pattern (CSP) algorithm and a corresponding feature, and computing mutual information of each corresponding feature with respect to one or more motor imagery classes;
    for each segment, summing the mutual information of all the corresponding features with respect to the respective classes, and
    selecting the corresponding features of the segment with a maximum sum of mutual information for one class for training.

17. The method as claimed in claim 16, further comprising training classifiers of the classification algorithm using the corresponding features after the corresponding features have been selected by the trained classification algorithm.

18. The method as claimed in claim 17, wherein training the classifiers comprises performing non-linear regression using the corresponding features after the corresponding features have been selected by the trained classification algorithm and performing non-linear post-processing regression using an output from the non linear regression.

19. The method as claimed in claim 16, wherein computing the spatial filtering projection matrix based on the CSP algorithm comprises using a multi-modal multi-time segment for each frequency band.

20. The method as claimed in claim 19, wherein the multi-modal multi-time segment for each frequency band comprises a multi-modal representation of idle states.

* * * * *